United States Patent [19]

Kossoff et al.

[11] 4,408,492

[45] Oct. 11, 1983

[54] SIGNAL PROCESSING EQUIPMENT FOR ULTRASONIC VISUALIZATION

[75] Inventors: George Kossoff, Northbridge; David E. Robinson, Bilgola Plateau, both of Australia

[73] Assignee: The Commonwealth of Australia, Phillip, Australia

[21] Appl. No.: 269,057

[22] PCT Filed: Sep. 19, 1980

[86] PCT No.: PCT/AU80/00070
§ 371 Date: May 13, 1981
§ 102(e) Date: May 13, 1981

[87] PCT Pub. No.: WO81/00807
PCT Pub. Date: Apr. 2, 1981

[51] Int. Cl.³ .............................................. G01N 29/04
[52] U.S. Cl. ...................................................... 73/631
[58] Field of Search ................. 73/631, 599, 602, 900, 73/626; 128/660

[56] References Cited

U.S. PATENT DOCUMENTS

| | | | |
|---|---|---|---|
| 3,690,153 | 9/1972 | Matay | 73/631 |
| 4,057,049 | 11/1977 | Hill | 73/570 |
| 4,140,107 | 2/1979 | Lancee et al. | 73/626 |
| 4,228,688 | 10/1980 | Sharpe | 73/631 |
| 4,305,296 | 12/1981 | Green et al. | 73/626 |

Primary Examiner—Anthony V. Ciarlante

[57] ABSTRACT

In megahertz ultrasonic echoscopy of objects, echoscopes having a time gain compensation facility are often used. To ensure that a uniform ultrasonic echo signal is obtained at a predetermined depth (5) within an object, the present invention varies the sensitivity of the time gain compensation for each pulse of ultrasonic energy (8) used to obtain an echogram of the object. The present invention may include means to vary the slope of the time gain compensation so that at other predetermined depths (6) within the object, echo signals of respective intensities are received, thus overcoming problems due to shadowing by ultrasonically highly absorbing regions of the object. The main application of the invention is in medical diagnosis.

9 Claims, 3 Drawing Figures

SIGNAL PROCESSING EQUIPMENT FOR ULTRASONIC VISUALIZATION

TECHNICAL FIELD

This invention concerns ultrasonic echoscopy. In particular it concerns the control of time gain compensation in ultrasonic echoscopy apparatus to improve the information content of echograms. This is particularly valuable in medical diagnosis using ultrasonic echoscopy, as it results in the more effective acquisition of relevant information, but the invention is not limited to this application of echoscopy.

BACKGROUND ART

To appreciate the nature of the present invention, it is helpful to first discuss the general principles of ultrasonic echoscopy (which is also known as ultrasonic echography, though strictly the two terms have different meanings). In ultrasonic echoscopy a short pulse of ultrasonic energy, typically in the 1–30 MHz frequency range, is directed into an object to be examined and any acoustic impedance discontinuities in the object reflect some of the energy. The reflected energy, or echo, is converted into an electrical signal and displayed on a cathode ray oscilloscope, a film, a chart, or in any other convenient form. This display, which provides information about the examined object to the user of the equipment, is known as an echogram.

The echogram may be either a one dimensional or a two dimensional representation. In both cases, the information is contained in the position and magnitude of the echo displayed. In a one dimensional display, the position along a base line is used to indicate the distance to the reflecting surface whilst the magnitude of the echo is displayed, for example, as a deflection of a base line or as an intensity change. In a two dimensional display, the position along a base line is used to indicate the distance to the reflecting surface as in a one dimensional display, and the direction of the base line is used to represent the direction of propagation of the acoustic energy. The two dimensional display is obtained by changing this direction of propagation of the acoustic energy and by instituting a similar, but not necessarily identical, movement of the base line of the display. The magnitude of the echo is displayed as for a one dimensional display (for example, as a deflection of the base line or as an intensity change).

The technique of ultrasonic echoscopy is used in medical diagnosis to obtain information about the anatomy of patients. The application of the technique has been described, for example, in the paper by D. E. Robinson in the "Proceedings of the Institution of Radio and Electronics Engineers, Australia", Volume 31, No. 11, pages 385–392, November, 1970, entitled "The Application of Ultrasound in Medical Diagnosis". As pointed out in that paper, ultrasonic echoscopy may be used to produce displays resembling anatomical cross-sections, and such displays have proved clinically useful when the desired information concerns the physical dimensions or the shape of organs, structures and the like. Ultrasonic echography has proved of particular value as a diagnostic aid in those areas of the body which contain soft tissue with little bone and air, particularly the abdomen and pregnant uterus, eye, breast, brain, lung, kidney, liver and heart. In general, the technique is considered to complement other techniques to provide a more complete picture of the patient's condition. However, particularly in pregnancies, ultrasonic echoscopy may be useful in place of X-rays as the latter may not give sufficient information, or may be dangerous.

Although ultrasonic echoscopy has uses other than as a diagnostic aid, this medical application of the technique provides a convenient example and will be used in the continuation of this description. In practice, a pulse of ultrasonic energy is transmitted into a patient in a known direction and echoes are received from reflecting surfaces within the body. The time delay between a transmitted pulse and the received echo depends on the distance from the transmitter to the reflecting surface and the distance information so obtained may be displayed in a suitable way for interpretation and clinical use as a one dimensional range reading or as a two dimensional cross-section as previously described. Now, when a pulse of ultrasound is propagated into any medium, echoes will be received at various time delays, which are proportional to the distances from the transducer producing the pulse to the reflecting surface if the velocity of propagation of ultrasound in the medium is constant. In soft tissues found in the human body, the velocity of sound is reasonably constant and pulsed ultrasound provides a convenient method of measuring the depth of a particular structure from the transducer face without inconvenience to the patient. This information can be used in a number of ways.

In the simplest form of display, known as "A mode", the echoes are presented as deflections of the trace of an oscilloscope, with distance being represented along the time axis. This mode is useful clinically when the source of the various echoes displayed can be positively identified. It is possible to measure the distance between two echoes, or between the energising pulse and an echo, with accuracy but it may not be possible to identify the source of the echoes. It has been used to measure the size of the baby's head inside the uterus, the depth of the eye and the bladder, and to locate the midline of the brain. Similar information may be displayed by use of the "B mode" display, which is a cross-sectional view obtained by moving the transducer around the examined object and making the trace on the display follow a similar movement. Both A and B mode displays may be obtained with either simple or compound scanning. With simple scanning, the movement of the transducer is selected so that there is no superpositioning of lines of sight from the different directions. Linear and sector scanning are typical examples of simple scanning. With compound scanning, the movement of the transducer is selected so that there is superposition from different lines of sight. A combination of linear and sector scanning is one example of a compound scan.

If the reflecting surface (or interface) of interest is moving, its position may be plotted with time ("M mode") by using the B mode presentation and allowing the time base to be swept at right angles to its direction so as to display the movements of the interface echo backwards and forwards along the time base. This technique has been used to demonstrate the pulsatile movements of various parts of the heart and brain. If the B mode is used but the trace on the screen is made to represent the line of sight of the transducer, and then the transducer is scanned around the patient and the time base line on the screen made to follow, a two dimensional plot of impedance discontinuities is obtained.

Two dimensional visualisation has been used in the pregnant uterus, abdomen, eye and breast.

Coupling from the transducer to the patient may be achieved by skin contact or by use of a water delay bath. If a water delay bath is used, the distance between the transducer and the skin surface must be greater than the largest depth of penetration to be used, to avoid ambiguity due to multiple reflections. In general, the skin contact scan results in greater comfort for the patient but echograms of less clarity, while the water delay scan gives less patient comfort and better quality echograms.

In order to compensate for the reduction in the energy of the ultrasonic pulse due to attenuation within the object under examination (for example tissue), the gain of the receiver is generally increased as the echo of the pulse is received from deeper reflecting surfaces within the object. This type of increase in gain is generally referred to as "time gain compensation" or "TGC". When using the echoscope equipment, the operator adjusts the sensitivity and slope of the TGC controlled amplifier after the first scan of a patient, then rescans the patient to obtain an image which is satisfactory for diagnosis. The gain controlled signals are then further processed and displayed in one of the ways described above.

In some receivers, TGC amplification is also followed by a non-linear compression amplification to further compress the size of the echoes so that they may be more readily displayed on the display unit. As the compression and display systems are non-linear, only qualitative information on echo size is displayed.

One deficiency of most examples of the apparatus that has hitherto been used in ultrasonic echoscopy is that the characteristics of the TGC control remain constant for the entire scan. This means that no account can be taken of local variation in tissue properties. This creates a problem because a local area, such as a bone or an air containing region, which is more highly absorbing than the surrounding tissue, casts an ultrasonic "shadow" which obscures deeper lying information.

One recent attempt to overcome the problem of variation in attenuation of signals within human tissue is described in the specification of U.S. Pat. No. 4,008,713 to J. M. Griffith and W. L. Henry. In the technique described in that specification, an amplifier of the received ultrasonic echo signals is switched rapidly from a high gain mode to a low gain mode to enable a particularly strong echo signal to be recognised from among a number of echo signals from the general region of the strong echo signal. This technique is shown to be applicable to echoscopy of the human heart, where it is important, when looking at the left ventricle, to be able to obtain information about the wall thicknesses of the cardiac structures, and to define accurately the location of the epicardial-lung interface. The septal and endocardial echoes are observed with a high gain amplification, while the epicardial signals are observed with low gain amplification. Such a technique is very limited in its application, and does not overcome the problem of "shadowing", which has been discussed above.

A system in which the gain of an amplification circuit is adjusted to compensate for various factors (absorption, "spreading", and interface reflection and scatter) is described in the specification of U.S. Pat. No. 4,043,181 to A. K. Nigam. One of the components of Nigam's amplification circuit is a time gain compensation unit, which is described in the passage from column 5, line 61 to column 6, line 22. It is clear from the description at column 6, lines 3 to 22 and column 8, lines 55 to 62, of specification No. 4,043,181 that Nigam's TGC unit involves the selection of a single attenuation factor, based on an average absorption value of the object under investigation. Thus Nigam's approach does not overcome the problem of "shadowing".

The specification of U.S. Pat. No. 4,057,049 to C. R. Hill does disclose a method of overcoming the problem of shadowing by adjusting the time gain compensation of the amplifier of received echo signals after determining the instantaneous attenuation values. However, the method used by Hill is rather complex, involving the measurement of the difference in values of the reflected echo signal at two frequencies. This difference is then used to automatically and instantaneously adjust the gain of the amplifier.

DISCLOSURE OF THE INVENTION

It is an object of the present invention to provide improved methods and apparatus in which control of TGC enables the problem of shadowing to be substantially overcome.

To achieve this objective, means are provided (a) to alter the TGC setting automatically, during the course of receipt of echoes of an ultrasonic pulse, in accordance with a certain set of constraints, to provide an improvement in image quality and the amount of information available to the interpreter of the images, and/or (b) to determine the TGC slope setting to compensate for attenuation within the region being examined and to display this setting.

According to the present invention, a method of ultrasonic examination of an object comprises subjecting the object of ultrasonic examination by an echoscope having a time gain compensation facility, characterised by the steps of:
(a) directing a first pulse of ultrasonic energy into the object;
(b) monitoring the intensity of a reflected ultrasonic signal from a given contour within the object;
(c) determining the sensitivity of the time gain compensation that is necessary for the reflected signal to have a predetermined intensity;
(d) adopting the determined time gain compensation;
(e) directing a second pulse of ultrasonic energy into the object to produce an echoscope display of the object; and
(f) repeating steps (a) to (e) until a complete echogram is obtained.

Also according to the present invention, a method of ultrasonic examination of an object comprises subjecting the object to ultrasonic examination by an echoscope having a time gain compensation facility characterized by the steps of:
(a) directing a first pulse of ultrasonic energy into the object;
(b) monitoring the intensity of a first reflected ultrasonic signal from a first predetermined contour within the object, and the intensity of a second reflected ultrasonic signal from a second predetermined contour within the object;
(c) determining the sensitivity of the time gain compensation value that is necessary to ensure that the first reflected signal has a predetermined intensity;
(d) determining the attenuation exhibited between the first and second contours;

(e) adopting the determined time gain compensation of step (c) and the slope of the time gain compensation that is necessary to compensate for the determined attenuation of step (d);

(f) directing a second pulse of ultrasonic energy into the object to produce an echoscope display thereof using the adopted time gain compensation and slope thereof of step (e); and (g) repeating steps (a) and (f) until a complete echogram is obtained.

It will be clear to those skilled in this art that the form of the invention recited in the last preceding paragraph is a modified form of the invention recited in the paragraph which precedes it.

In a variation of the form of the present invention in which two reflected echo signals are observed, the step (g) can be omitted and the complete echogram scan can be carried out with the determined time gain control values of step (c) and the determined attenuation values of step (d) stored in a memory device, whereby the complete echogram can be constructed using the stored values of the time gain compensation for each signal of the scan and an average time gain compensation slope value derived from the average of the stored attenuation values. With this modification, the average value of the attenuation of the material located between the first and second predetermined depths can be displayed to the operator of the echoscope, or the appropriate diagnostician.

It will be appreciated that a "complete echogram" refers to a required echogram, and may, in practice, be an echogram of only part of the object being observed.

Further according to the present invention, an ultrasonic examination apparatus having a time gain compensation facility (a) ultrasonic transmission means for transmitting pulses of ultrasonic energy into an object;

(b) means for selecting ultrasonic signals reflected from at least two predetermined contours within said object;

(c) intensity monitoring means for monitoring the intensity of each reflected signal from within said object; and (d) means responsive to said intensity monitoring means for varying the time gain compensation of the time gain compensation facility while effecting an echogram of said object: is characterized in that the intensity monitoring means is a programmed computer which evaluates, for a sequence of reflected ultrasonic signals, (i) the sensitivity of the time gain compensation necessary for the reflected signals from all parts along the first predetermined contour within the object to have a predetermined density, and (ii) an average value of the time gain compensation slope between each signal reflected from the first and the second or any other predetermined contour within the object to ensure that the signal from the second or other predetermined contour has an associated predetermined value.

BEST MODES OF CARRYING OUT THE INVENTION

Figure 1:
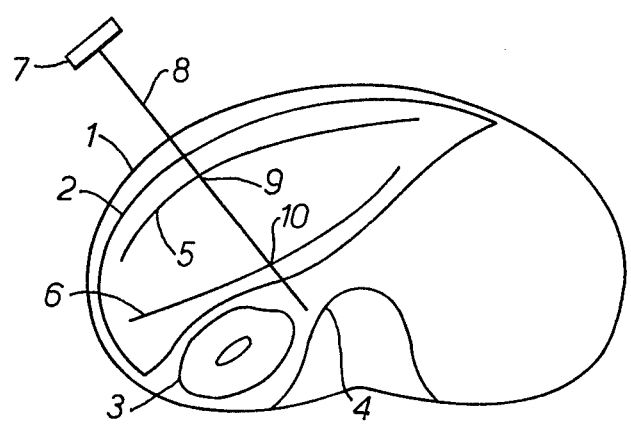
FIG. 1 is a diagrammatic representation of the taking of a transverse echogram of the human body at the level of the liver.

In FIG. 1 an outline of the body 1 is shown in transverse cross section at the region of the abdomen viewed from below, as is customary in the art. The top of the Figure represents the anterior side or front of the body and the left-hand side of the Figure is on the patient's right. Inside the abdomen is the liver 2. The space between the outer skin of the body at 1 and the liver 2 contains the anterior wall of the body which may include muscle, fat layers and ribs. Also represented are the right kidney 3 and vertebral column 4.

When obtaining an echogram of the liver tissue, an operator has to scan across the ribs. Each rib causes some attenuation and casts a shadow which projects across the liver and interferes with diagnosis. To overcome the effects of the shadow, the present invention is utilised. After a first echoscope image (echogram) of the liver is obtained, the operator defines one or two lines or contours 5, 6 on the image. Line 5 is located at an even depth below the skin surface but wholly within the liver volume. If a second line 6 is defined, it is located near the posterior boundary of the liver. An ultrasonic transducer 7 used to form the echogram image when located as shown in FIG. 1, has a line of sight 8 which intersects lines 5 and 6 (if defined) at points 9 and 10 respectively. The echogram is then reconstructed with the sensitivity of the amplifier for each ultrasound line of sight being readjusted so that the signal level at the position of the defined line 5 is constant. In this way the effect of the shadowing by the rib is removed from the echogram.

If the second line 6 has been defined on the image, when the echogram is reconstructed, for each line of sight, the values of reflected signal level from points 9 and 10 are corrected for the distance between the two lines 5, 6 along the ultrasonic beam. From the correction signal, an effective attenuation per unit distance can also be determined. If this attenuation is measured for all of the lines of sight which traverse the liver, an average value of attenuation per unit distance can be derived and can be used to establish a TGC slope setting so that when the image is once again reconstructed (using the TGC slope which has been derived), the echogram is compensated for the attenuation of the particular liver which is being scanned. The average attenuation figure derived can also be made available to the interpreter of the echoscope display as a further piece of diagnostic information.

Figure 2:
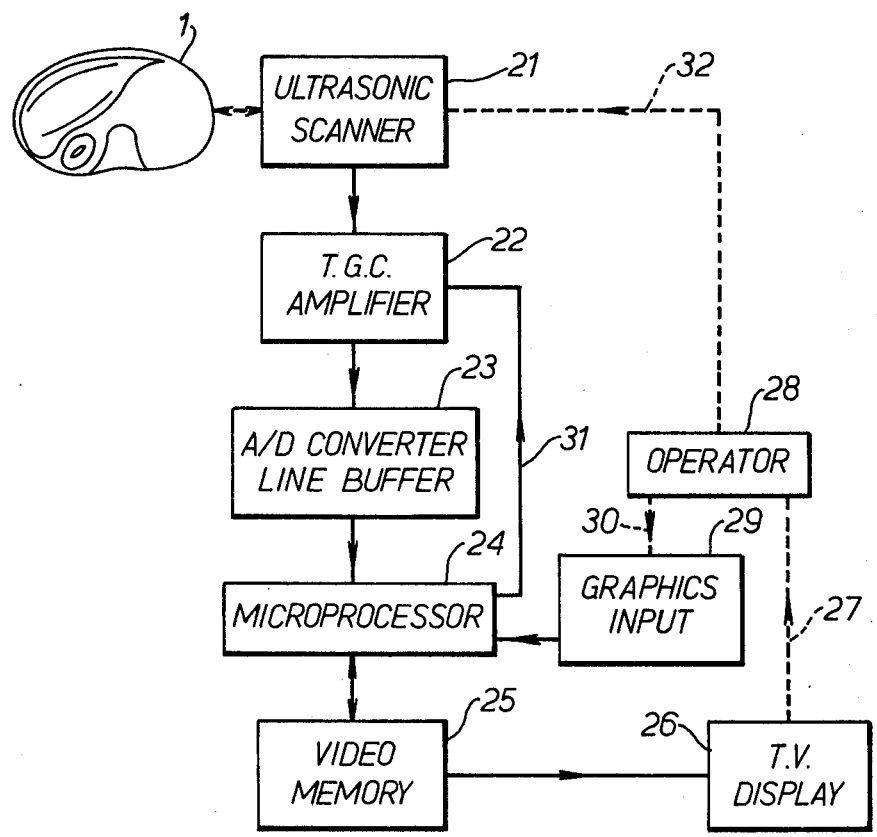
FIG. 2 is a block diagram of one embodiment of the apparatus of the present invention, in which the data is reacquired for each component location of the echogram.

One form of apparatus for performing the method of the present invention is illustrated in FIG. 2. The basic component of this apparatus is a digital scan converter which is well known in the art. The echogram is formed by the operation of an ultrasonic scanner 21 which is used to examine a patient 1. Received ultrasonic echo signals from the scanner are fed to a time gain control amplifier 22, the output of which is supplied to an analogue to digital converter and single line memory 23. A microprocessor and digital logic 24 converts the echoes along the ultrasonic line of sight into corresponding intensity values at the appropriate co-ordinates in the output image, and these values are stored in video memory 25 and displayed on a TV display 26. The analogue to digital converter 23, microprocessor 24 and video memory 25, in combination, form a digital scan converter. To perform the present invention, information is passed from the TV display 26 through an optical path 27 to the operator 28 who operates a graphics input unit 29 through a manual control path 30 to define the required lines 5 and 6 of FIG. 1 to the microprocessor 24 and on to the TV display 26.

To effect shadow removal, as already noted, only the anterior line 5 in FIG. 1 is required. After line 5 is input through the graphics input 29, the operator 28 activates the ultrasonic scanner 21 through manual control path 32. The ultrasonic scanner 21 rescans the patient 1. For the first line of sight (corresponding, for example, to line 8 of FIG. 1), echoes are received, amplified in TGC amplifier 22 and converted to digital form in the analogue to digital converter and line buffer 23. The microprocessor 24 identifies the distance along the line of sight 8 corresponding to the intersection point 9 with the defined line 5. The microprocessor 24 then determines the energy around the point 9 and calculates a correction value to make it equal to a preset energy. The micro-processor then readjusts the sensitivity setting of the TGC amplifier 22 via the control path 31. Another ultrasonic pulse is transmitted by the ultrasonic scanner 21 along the same line of sight 8 and the received echoes are fed down the signal chain as before through elements 22, 23 and 24 using the new TGC amplifier settings. This process is repeated for each ultrasonic line of sight to construct a new ultrasonic echogram in which the echoes lying along defined line 5 are equal in all lines of sight.

To perform the additional step of determining the average attenuation in the liver tissue, the first echogram is formed and the lines 5 and 6 are defined on it in the manner described above. The operator 28 then initiates a second scan of the patient by ultrasonic scanner 21. For each line of sight in this scan, the microprocessor 24 determines the appropriate points 9 and 10 on each line of sight 8 and derives, from the echo energy at each point and the distance between points 9 and 10 along the line of sight 8, the value of the attenuation (which is normally expressed in decibels per centimeter). This procedure is repeated for all the lines of sight which go to form the echogram and which intersect the two lines 5 and 6, and from all the results, an averaged value of the attenuation is calculated. This averaged value is then used to derive a fresh slope value for the TGC amplifier, which is readjusted by control path 31. The operator 28 then initiates a third scan by ultrasonic scanner 21 and a new echogram is formed with the correct TGC amplifier settings as derived from the previous procedures described above.

It will be clear to one skilled in the art that these two procedures may be combined to automatically adjust both the sensitivity and slope of the TGC control.

Figure 3:
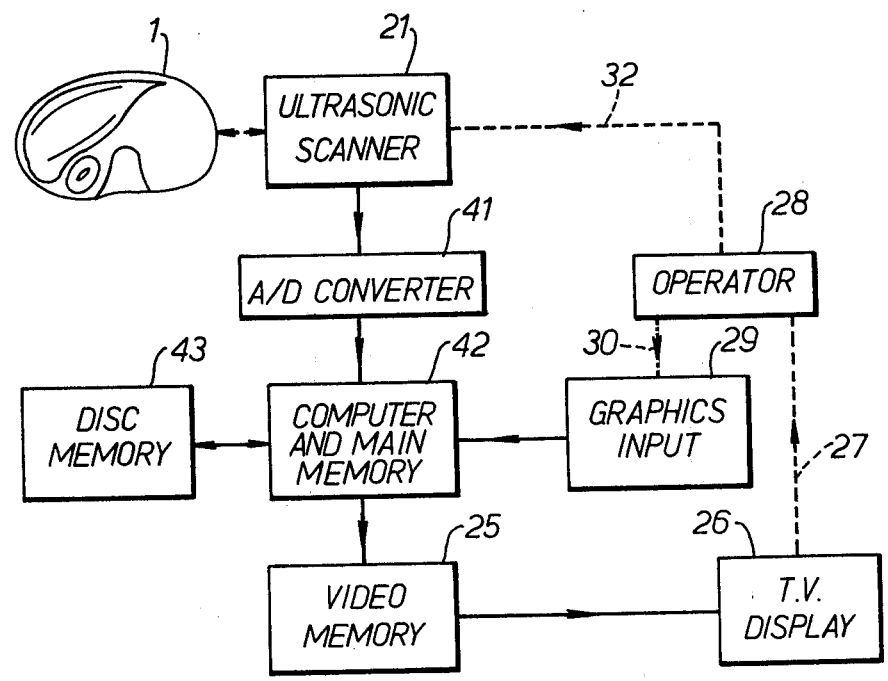
FIG. 3 is a block diagram of a second embodiment of the apparatus of the present invention, in which the data obtained is stored in a digital disc memory at its first acquisition.

In another application of the present invention, which uses the apparatus depicted in FIG. 3, a digital computer is used. Signals from the ultrasonic scanner 21 are amplified and fed directly through analogue to digital converter 41 into the computer 42. All the lines that go to make up the echogram are stored immediately on disc memory 43. The echogram is reconstructed from the data stored on the disc memory and output to the video memory 25 and the TV display 26. The defined lines 5 and 6 are input through the same graphics terminal 29 to the computer and the same steps that were used in the digital scan converter case described with reference to FIG. 2 are then carried out. However, because all of the data is stored line by line on the disc memory, there is no need to rescan the patient as all the operations can be carried out digitally in the computer, using the stored data.

Persons skilled in electronic circuit design will be aware of the existence of various analogue to digital converters, memories, and programmable microprocessors which may be used in the circuits illustrated in FIGS. 2 and 3. In addition, persons skilled in echoscopy will appreciate that although reflections from only two depths within an object have been featured in the embodiments of the invention described above, the same concepts may be applied with reflected signals from more than two depths, improving the average attenuation values which are computed. The only disadvantage in such an extension of the invention is an increased complexity and cost of the equipment required.

INDUSTRIAL APPLICABILITY

Medical diagnosis has been referred to exclusively in the embodiments of the present invention described above. This is because medical diagnosis represents the main current application of the present invention. However the invention is certainly not limited to medical diagnosis alone.

We claim:

1. A method of ultrasonic examination of an object comprising subjecting the object to ultrasonic examination by an echoscope having a time gain compensation facility, characterized by the steps of:
   (a) directing the first pulse of ultrasonic energy into the object;
   (b) monitoring the intensity of a reflected ultrasonic signal from a given contour within the object;
   (c) determining the sensitivity of the time gain compensation that is necessary for the reflected signal to have a predetermined intensity;
   (d) using in said time gain compensation facility the determined time gain compensation;
   (e) directing a second pulse of ultrasonic energy into the object to produce an echoscope display of the object; and
   (f) repeating steps (a) to (e) until a complete echogram is obtained.

2. A method of ultrasonic examination of an object comprising subjecting the object to ultrasonic examination by an echoscope having a time gain compensation facility, characterized by the steps of:
   (a) directing a first pulse of ultrasonic energy into the object;
   (b) monitoring the intensity of a first reflected ultrasonic signal from a first predetermined contour within the object, and the intensity of a second reflected ultrasonic signal from a second predetermined contour within the object;
   (c) determining the sensitivity of time gain compensation value that is necessary to ensure that the first reflected signal has a predetermined intensity;
   (d) determining the attenuation exhibited between the first and second contours;
   (e) using in said time gain compensation facility the determined time gain compensation of step (c) and the slope of the time gain compensation that is necessary to compensate for the determined attenuation of step (d);
   (f) directing a second pulse of ultrasonic energy into the object to produce an echoscope display thereof using the adopted time gain compensation and slope thereof of step (e) and;

(g) repeating steps (a) to (f) until a complete echogram is obtained.

3. A method of ultrasonic examination of an object comprising subjecting the object to ultrasonic examination by an echoscpe having a time gain compensation facility, characterized by the steps of:

(a) directing a first pulse of ultrasonic energy into the object;

(b) monitoring the intensity of a first reflected ultrasonic signal from a first predetermined contour within the object, and the intensity of a second reflected ultrasonic signal from a second predetermined contour within the object;

(c) determining the sensitivity of the time gain compensation value that is necessary to ensure that the first reflected signal has a predetermined intensity;

(d) determining the attenuation exhibited between the first and second contours;

(e) storing the determined value of the attenuation of step (d) in a memory;

(f) repeating steps (a) to (e) for each pulse of the sequence of ultrasonic energy pulses required to effect a complete echogram of the object;

(g) deriving, from the entire stored values of atenuation in said memory, an average value of attenuation between the first and second contours and an average value of the slope of the time gain compensation required to compensate therefor; and (h) directing a second sequence of pulses to effect a complete echogram into the object, and using the determined time gain compensation for each pulse of step (c) and the average slope of the time gain compensation, obtaining a complete echogram of the object.

4. A method of ultrasonic examination of an object comprising subjecting the object to ultrasonic examination by an echoscope having a time gain compensation facility, characterized by the steps of:

(a) directing a first pulse of ultrasonic energy into the object;

(b) monitoring the intensity of a first reflected ultrasonic signal from a first predetermined contour within the object, and the intensity of a second reflected ultrasonic signal from a second predetermined contour within the object;

(c) determining the sensitivity of the time gain compensation value that is necessary to ensure that the first reflected signal has a predetermined intensity;

(d) determining the attenuation exhibited between the first and second contours;

(e) storing each monitored value of intensity of step (b) and the determined values of the sensitivity of step (c) and the attenuation of step (d) in a memory;

(f) repeating steps (a) to (e) for each pulse of the sequence of ultrasonic energy pulses required to effect a complete echogram of the object;

(g) deriving from the entire stored values of the intensitites, the sensitivities and the attenuations in said memory, a complete echogram of said object.

5. A method of ultrasonic examination of an object using an echoscope having a time gain compensation facility, as defined in any one of claims 2,3 and 4 characterised in that step (b) is changed to the step of monitoring the intensities of a plurality of reflected ultrasonic signals from respective predetermined depths within said object.

6. An ultrasonic examination apparatus having an echoscope display resolution circuit with a time gain compensation facility comprising:

(a) ultrasonic transmission means for transmitting pulses of ultrasonic energy into an object;

(b) means for selecting ultrasonic signals reflected from at least one predetermined contour within the object;

(c) intensity monitoring means for monitoring the intensity of the or each reflected signal; and (d) means responsive to said intensity monitoring means for varying the time gain compensation of the time gain compensation facility;

characterized in that:

(i) said means for selecting reflected ultrasonic signals receives reflected signals from the consecutive pulses of ultrasonic energy from said transmission means from each point on said at least one contour;

(ii) the reflected signal or signals from the first of said two consecutive pulses is used to change the time gain compensation of the time gain compensation facility to compensate for the attenuation of reflected signals at said or each predetermined contour such that the signal level is constant along the or each contour; and (iii) the reflected signal or signals from the second of said consecutive pulses is used to produce an echogram of said object.

7. An ultrasonic examination apparatus as defined in claim 6, further characterized in that said means responsive to said intensity monitoring means comprises, in combination, a memory for storing each value of intensity monitored by said intensity monitoring means, and a microprocessor programmed to transfer information to and retrieve information from said memory and to evaluate the sensitivity of the time gain compensation necessary for said or the first of said reflected signals to have a predetermined intensity.

8. An ultrasonic examination apparatus having a time gain compensation facility comprising:

(a) ultrasonic transmission means for transmitting pulses of ultrasonic energy into an object;

(b) means for selecting ultrasonic signals reflected from at least two predetermined contours within said object;

(c) intensity monitoring means for monitoring the intensity of each reflected signal from within said object; and (d) means responsive to said intensity monitoring means for varying the time gain compensation of the time gain compensation facility while effecting an echogram of said object;

characterized in that said intensity monitoring means comprises a computer programmed to evaluate, for a sequence of reflected ultrasonic signals, (i) the sensitivity of the time gain compensation necessary for the reflected signals from all parts along the first predetermined contour within said object to have a predetermined intensity, and (ii) an average value of the time gain compensation slope between each signal reflected from the first and the second or any other predetermined contour within said object to ensure that the signal from the second or other predetermined contour has an associated predetermined value.

9. An echoscope display resolution circuit as defined in any one of claims 6, 7 or 8 further characterized in that said means to select ultrasonic signals includes a graphics input unit.

* * * * *